United States Patent
Xie et al.

(10) Patent No.: US 9,462,183 B2
(45) Date of Patent: Oct. 4, 2016

(54) TRIGGER FOR BLADE IMAGING BASED ON A CONTROLLER

(75) Inventors: Binglong Xie, Lawrenceville, NJ (US); Yakup Genc, Dayton, NJ (US); Frank Dierkes, Aachen (DE)

(73) Assignee: Siemens Energy, Inc., Orlando, FL (US)

( * ) Notice: Subject to any disclaimer, the term of this patent is extended or adjusted under 35 U.S.C. 154(b) by 436 days.

(21) Appl. No.: 13/531,658

(22) Filed: Jun. 25, 2012

(65) Prior Publication Data

US 2013/0162846 A1 Jun. 27, 2013

Related U.S. Application Data

(60) Provisional application No. 61/537,633, filed on Sep. 22, 2011.

(51) Int. Cl.
| | |
|---|---|
| *H04N 5/232* | (2006.01) |
| *F01D 21/00* | (2006.01) |
| *G01N 21/88* | (2006.01) |
| *G01N 21/954* | (2006.01) |

(52) U.S. Cl.
CPC ........ *H04N 5/23222* (2013.01); *F01D 21/003* (2013.01); *G01N 21/8806* (2013.01); *G01N 21/8851* (2013.01); *F05D 2230/72* (2013.01); *G01N 21/954* (2013.01); *G01N 2021/8838* (2013.01)

(58) Field of Classification Search
CPC H04N 5/23222; H04N 5/232; F01D 21/003; G01N 21/8806; G01N 21/8851; G01N 21/954; G01N 2021/8838; F05D 2230/72
USPC ............ 348/82, 92, 207.11; 415/1; 123/438; 156/64
See application file for complete search history.

(56) References Cited

U.S. PATENT DOCUMENTS

| 3,783,058 A | * | 1/1974 | Solomon et al. ................ 156/64 |
|---|---|---|---|
| 5,033,305 A | * | 7/1991 | Rozelle et al. .................. 73/650 |
| 5,275,052 A | * | 1/1994 | Luttrell .............. G01N 29/0645 |
| | | | 73/619 |
| 7,064,811 B2 | | 6/2006 | Twerdochlib |

(Continued)

FOREIGN PATENT DOCUMENTS

| CN | 1800844 A | 7/2006 |
|---|---|---|
| CN | 102192914 A | 9/2011 |
| JP | 2007013961 A | 1/2007 |

OTHER PUBLICATIONS

"Tachometer signal conditioner and once-per-revolution pulse extractor", *Vibro-Meter OPR 706*, 6 pgs.

(Continued)

*Primary Examiner* — Jay Patel
*Assistant Examiner* — Neil Mikeska (57) ABSTRACT

A rotating rotor in a turbine has blades attached. At least one blade is a reference blade of which a reference position is determined by a Once-Per-Rotation sensor. A camera positioned at a viewing port takes a sequence of images of all the blades during a rotation at a trigger moment determined by a controller. The controller receives a signal indicating that the reference blade passes its reference point. The controller is provided with data about the number of blades, the position of the camera and a desired dwell of an image related to the blade. The controller calculates the trigger moments and generates trigger signals to the camera. The trigger moment is adjusted for changing rotor speed by extracting a blade feature from blade images. The camera records images that are labeled and stored as image data on a storage device.

20 Claims, 9 Drawing Sheets

(56) References Cited

U.S. PATENT DOCUMENTS

| | | | | |
|---|---|---|---|---|
| 2003/0107815 A1* | 6/2003 | Redmond | ................... | 359/619 |
| 2004/0101023 A1 | 5/2004 | Choi | | |
| 2005/0276448 A1* | 12/2005 | Pryor | ........................ | 382/103 |
| 2006/0078193 A1 | 4/2006 | Landi | | |
| 2006/0098751 A1* | 5/2006 | Zhang et al. | ............... | 375/260 |
| 2007/0258807 A1 | 11/2007 | Brummel | | |
| 2009/0312956 A1* | 12/2009 | Zombo | ................ | F01D 5/288 702/34 |
| 2011/0211940 A1* | 9/2011 | George et al. | ................... | 415/1 |
| 2012/0321292 A1* | 12/2012 | Viglione et al. | ............ | 396/458 |

OTHER PUBLICATIONS

Lawson, Craig, "Capacitance Tip Timing Techniques in Gas Turbines", *Thesis* 2003, 223 pgs.
PCT International Search Report mailed Dec. 21, 2012 corresponding to PCT International Application No. PCT/US2012/052653 filed Aug. 28, 2012 (9 pages).
Translation of Chinese Office Action mailed Jul. 24, 2015 corresponding to Chinese Application No. 201280046117.2 filed Aug. 28, 2012 (25 pages).

* cited by examiner

TRIGGER FOR BLADE IMAGING BASED ON A CONTROLLER

STATEMENT OF RELATED CASES

The present application claims priority to and the benefit of U.S. Provisional Patent Application Ser. No. 61/537,633 filed on Sep. 22, 2011, which is fully incorporated herein by reference.

TECHNICAL FIELD

The present invention relates to obtaining images from rotating blades in a turbine.

BACKGROUND

Blades are mission critical parts for turbines. Such turbines have many uses, including those used for generating electricity. These turbines endure a difficult operating environment and require maintenance. During maintenance of the turbine it is useful to obtain images of the individual blades, for instance, to visually assess an amount of wear and tear.

It is believed that currently no systems or methods are available that enable a camera to take an image of a specific part of a rotating blade in a turbine.

Accordingly improved and novel methods and systems are required to have a camera record an image of a rotating blade in a turbine.

SUMMARY

In accordance with an aspect of the present invention, a method to determine a trigger moment for a controller controlled camera to record an image of a blade attached to a rotating rotor including a plurality of blades in a turbine, is provided. The method includes the steps of the controller determining a first trigger moment for the blade based on the plurality of blades, a preset dwell, a rotating speed of the rotating rotor and a position of the camera; the camera recording a first image of a first blade in the plurality of blades; the camera recording a second image of a second blade in the plurality of blades; the controller registering the first and second image based on an image feature to determine a time shift; and the controller determining the trigger moment for the blade from the first trigger moment adjusted based on the time shift.

In accordance with a further aspect of the present invention, the method also includes the step of the controller controlled camera recording an image of the blade based on a trigger signal on the trigger moment determined by the controller. The image feature can be extracted by using a feature extraction method from the group consisting of Canny edge detection, Harris corner detection, Harris-Affine interest point detection and SIFT. The position of a reference blade can be determined with a once-per-revolution (OPR) sensor.

In accordance with another aspect of the present invention, the method includes then step of the controller determining the trigger signal at each of a plurality of adjusted trigger moments and the controller controlled camera recording at least a single image of each of the plurality of blades during a single rotation of the rotating rotor at the plurality of adjusted trigger moments.

In accordance with a further aspect of the invention, each of the at least single image of each of the number of blades recorded during the single rotation of the rotating rotor is provided with a data label and is stored as an individually retrievable image on a data storage device.

In accordance with another aspect of the invention, the turbine is off-line and the rotating rotor is rotated by a motor. The rotating rotor can be controlled to rotate with a rotating speed of less than 12 revolutions per minute.

In accordance with a further aspect of the invention, the number of blades on the rotating rotor is less than 70.

In accordance with another aspect of the present invention, the controller maintains an actual dwell for each image of the plurality of blades within a single rotation of the rotor that is at least 10% accurate compared to the preset dwell.

The present invention also provides a system to implement the methods described herein. In the system a controller to trigger a camera to record an image of a blade attached to a rotating rotor with a plurality of blades in a turbine, is provided. The controller includes a memory to store data and a processor enabled to execute instructions to perform the steps of: determining a first trigger moment for the blade based on the plurality of blades, a preset dwell, a rotating speed of the rotating rotor and a position of the camera; the camera recording a first image of a first blade in the plurality of blades; the camera recording a second image of a second blade in the plurality of blades; the processor registering the first and second image based on an image feature to determine a time shift; and the processor determining the trigger moment for the blade from the first trigger moment adjusted based on the time shift.

Each of the above steps is performed by the controller.

These and other aspects of the invention are described in the following.

DESCRIPTION

Blades in a turbine are attached to a rotor which rotates about an axis. In accordance with an aspect of the present invention, an image is made of a blade while the rotor and thus the blade is moving. The image, in one embodiment of the present invention, is a still image or a picture. In accordance with an aspect of the present invention, the image is taken at the correct moment so that a desired part of the blade is within the field of view of the camera. This requires that the camera is activated at the correct time when the blade passes through the field of view of the camera.

Figure 1:
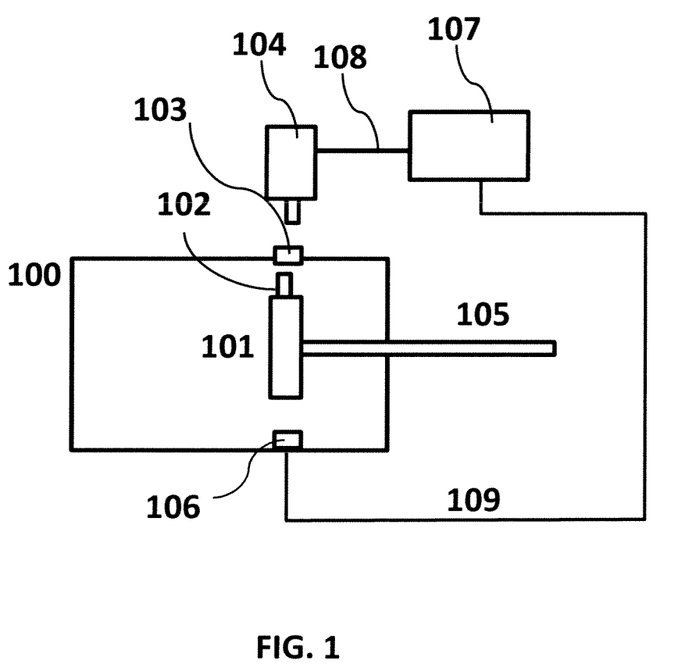
FIG. 1 illustrates a camera trigger system in accordance with various aspects of the present invention.

A set-up in accordance with an aspect of the present invention is illustrated in FIG. 1. A turbine 100 has a rotor 101 attached to an axis 105. Blades are attached to the rotor 101, of which one blade 102 is identified. A camera 104 with a lens is positioned to obtain blade 102 within its field of view when the rotor is turning and the blade passes through the camera's field once every revolution of the rotor. The camera is to be triggered to take an image of the blade at the correct moment that it is passing through the field-of-view.

In one embodiment of the present invention, the camera 104 is positioned at a viewing or observation port 103 in or through the turbine housing which allows viewing of the blades 102 on the rotor 101.

The camera 104 is connected to a controller 107 which controls controllable functions of camera 104 via a connection 108, which may be a wireless connection. In one embodiment of the present invention, the controller 107 is connected to a computer or a computer device 110. The computer device 110 can be used to program and control controller 107. Computer 110 also contains a data storage device such as a hard disk which may be used to store images generated by camera 104.

Among the controllable camera functions are (a) a shutter speed and (b) a moment of recording.

The camera 104 may be a camera for recording single images or still pictures or a video camera. The camera, in one embodiment of the present invention, is a digital camera with an image sensor, for instance a CMOS or CCD image sensor as is known in the art.

If the camera is a photo camera, then a trigger signal causes the camera to take at least a single picture at a moment determined by the trigger signal for instance by triggering a shutter, which may be a mechanical or an electronic shutter.

The situation is different when the camera is a video camera. In that case, when the camera is recording video images, in one embodiment of the present invention a continuous stream of video frames is being recorded. Assuming an electronic shutter system with, for instance, a global shutter, a series of images in video frames are recorded. The controller, in that case, identifies the frame which captures the required blade in the desired position. In one embodiment of the present invention, a video camera can be placed in an "individual frame trigger" mode. This means that the video camera generates a single image based on the trigger.

In both camera types, an image of a blade is generated. In case of a digital camera, image data of each image is stored in a data memory or a data storage device and provided with a label that identifies a position of the blade on the rotor and possibly other data such as the dwell or moment of recording or an ID related to a specific rotation. This allows each image of a blade to be retrieved individually from storage. In a further embodiment of the present invention, all blades on a rotation of the rotor are recorded during a rotor rotation and are labeled and stored associated with a specific dwell. One can then retrieve a sequence of blade images from the storage device based on at least one of possible labels, which may include time of recording, rotation speed of the rotor, and preset dwell of the images related to a predefined neutral position.

The controller 107 is connected via a connection 109 to a sensor 106 which is a Once-Per-Revolution (OPR) sensor, which provides a signal when a reference blade passes the sensor. OPR sensors in turbines are known. Such an OPR sensor may, for instance, be an optical sensor that detects a marking on a reference blade. Such a sensor may, for instance, also be a capacitance probe based tip clearance measurement system wherein a tip of a reference blade is extended and which is detected by a capacitance based sensor.

Figure 2:
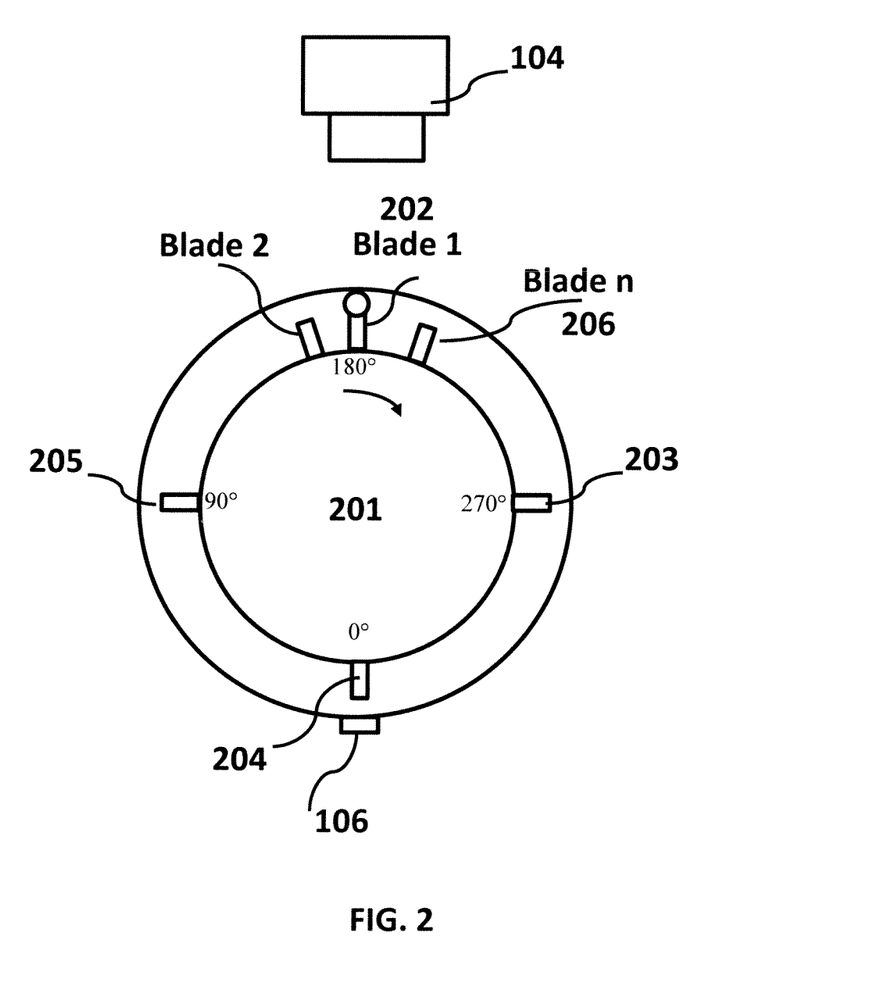
FIGS. 2-4 illustrate turbine blades in accordance with an aspect of the present invention.

FIG. 2 illustrates in further detail the rotor blades and the sensor. The blades are attached to the rotor 201. Blade 1 identified as 202 is the reference blade, and has become so by applying some modification, such as a marking of an extension or any other means such as a magnet for instance. The blades are observed by the camera 104. There are n blades on the rotor, evenly distributed along the rotor. For illustrative purposes blades 203, 204, 205 and 206, which is the last or nth blade and that is adjacent to the first blade. When blade 202 passes sensor 106 a sensor signal is generated to the controller.

The rotation time for the reference blade to complete one full revolution is T. The OPR sensor ticks once for each turn the turbine machine rotates. There are a fixed number of blades along the rotation direction, and a picture should be taken of each of them at the same offset, called dwell. The system of the present invention has a trigger controller that takes as input the OPR signal, and number of blades, and the dwell, and generates the triggers such that the camera captures exactly one picture at the specified dwell for each.

Figure 3:
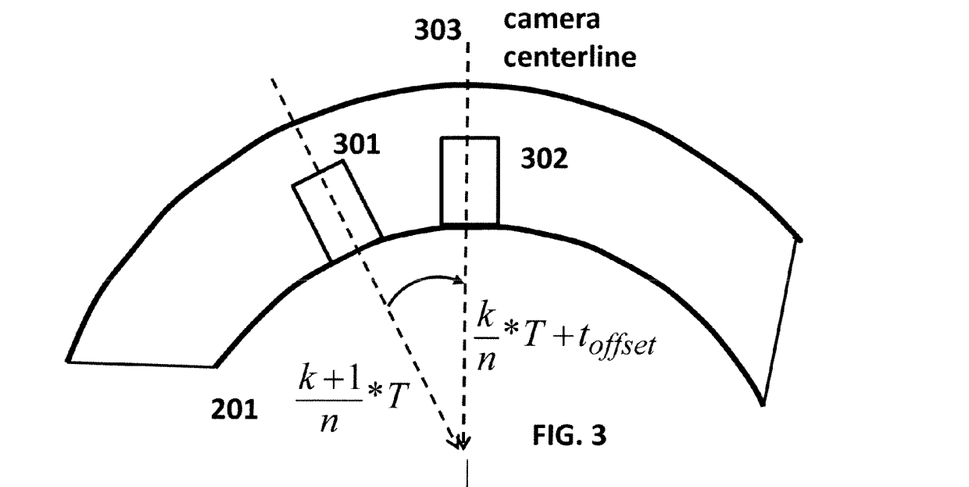

This is further illustrated in FIG. 3. The time it takes to move the rotor from a position in a first blade 302 to a similar position in a blade 301 is $$\frac{1}{n} * T.$$

Figure 4:
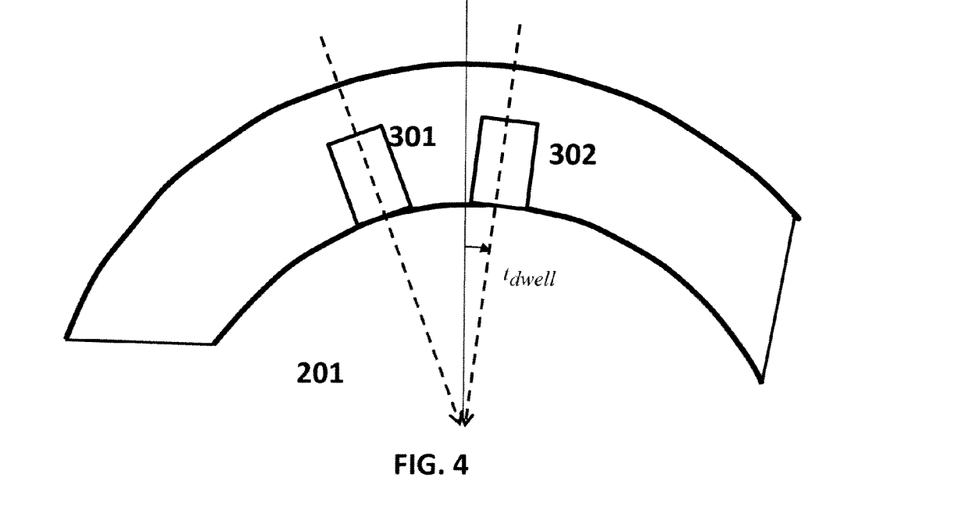

The camera is in a different position than the sensor, leading to an offset. FIG. 4 illustrates a small offset or dwell, which allows the blade to be recorded by the camera with a predefined offset from its central position.

In the zero position (when the OPR signal is generated) the positions in degrees of the kth of n blades in a 360 degrees polar system with $p_0(1)=0$ (the blade k=1 is the reference blade) can be expressed as $$p_0(k) = 360 - \frac{360}{n}(k-1) \bmod 360$$

in a clockwise rotating turbine rotor and a clockwise polar coordinate system, wherein all calculations are modulo 360, as illustrated in FIG. 2. The selected coordinate system is arbitrary and other coordinate systems and calculated positions can be applied.

The angular speed of the blades is $$v_{blade} = \frac{360}{T}.$$

The camera is in an angular position β relative to the position of the sensor, which is assumed to be in position 0. This means that after time $t_{cam}$ elapsed after t=0 when blade k=1 is detected by the OPR sensor the following expression applies:

$$\beta = \left(360 - \frac{360}{n}(k-1) + \frac{360}{T}t_{cam}\right) \bmod 360.$$

This allows a processor to determine time $t_{cam}$ for the condition when blade k is within the view of the camera.

One can adjust β for the deviation by the dwell angle $\alpha_{dwell}$ from the center or neutral position of the blade in the center of the camera view. If one wants to take a picture of the blade when it is within view of the camera, one takes a picture before the neutral position is used and one adjusts $\beta_{new}=\beta-\alpha_{dwell}$. Similarly, when one wants to take a picture after the blade has passed the neutral position one adjusts with $\beta_{new}=\beta+\alpha_{dwell}$.

In one embodiment of the present invention the dwell is set for each individual blades or for a group of blades.

The rotation period T is determined and updated every time the reference blade passes the OPR sensor 106. After every new calculation of T, all formulas and determinations of triggering moments for all blades are updated by the controller.

The following describes in detail an implementation for triggering a camera in a system for synchronized image capturing of blades in a turbine machine, using the Arduino controller board. The Arduino controller board is an open-source electronics proto-typing platform which is enabled to interact with the environment by receiving and processing external signals and generating control signals for external devices. Details related to the Arduino platform are known and published on, for instance, its website at URLwww.arduino.cc. While the Arduino platform is used and described herein for illustrative purposes, it is to be understood that any controller enabled to receive and process external signals and to control an external device with generated signals is enabled to perform the steps of methods, as provided herein in accordance with various aspects of the present invention.

In one embodiment of the present invention, the controller is connected to a computer, commonly through a USB port, to run or supervise the controller. In one embodiment of the present invention, a controller when provided with power can operate as an independent system.

Controllers are sometimes indicated as micro-controllers. A controller has a processor and memory and a series of input/output ports and is enabled and intended to control a device for which it is programmed. In general, it is dedicated to a specific device that is programmed once, in what is commonly indicated as firmware stored in a memory such as for instance ROMs or PROMs or the like. Before a controller is put in a device its control program is commonly developed on a development or a prototyping system that is generally controlled by a computer or a PC using some high level development language. The Arduino controller proto-typing system is an open source controller development system using for instance a controller marketed by Atmel Corporation of San Jose, Calif. Other prototyping or development systems are known.

In the system, the OPR sensor ticks once for each turn the turbine machine rotates. There are fixed number of blades along the rotation direction, and each of them should be taken a picture at the same offset, called dwell. The system has a trigger controller that takes as input the OPR signal, and number of blades, and the dwell, and generates the triggers such that the camera captures exactly one picture at the specified dwell for each.

Figure 5:
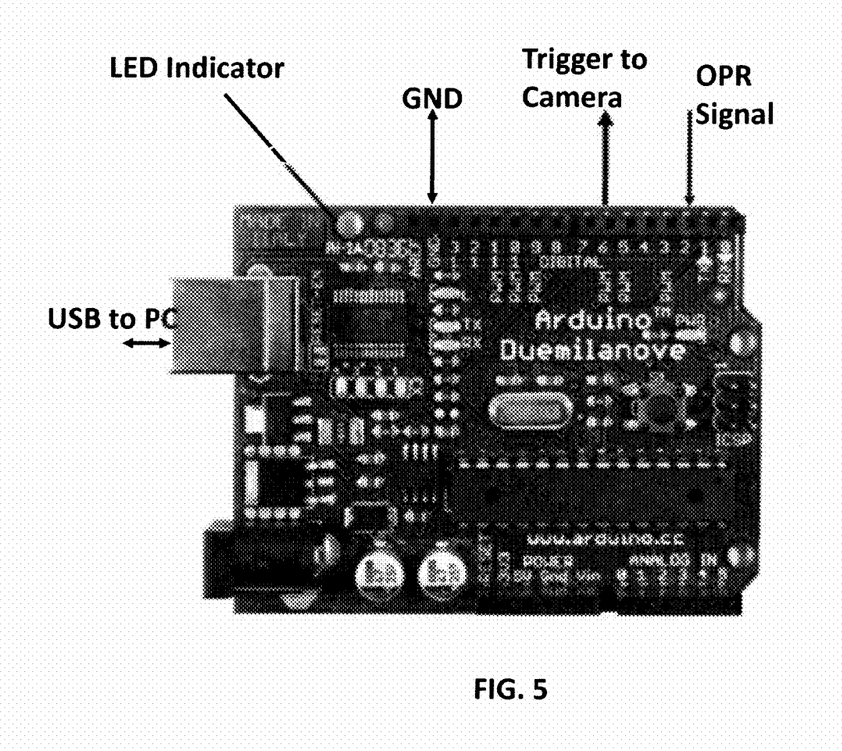
FIG. 5 illustrates a processor in accordance with an aspect of the present invention.

The trigger controller in an illustrative example is based on an Arduino controller board, for example, Arduino Duemilanove or Arduino Uno as illustrated in FIG. 5, including the firmware running onboard and software running in PC that communicates with the board. The OPR sensor is wired to a Pin 2. The trigger output to camera is provided at Pin 6. The Pin configuration is easily adjustable in software. The board is connected to PC using a USB cable, which also delivers power from the PC to the board.

Firmware

The firmware running on Arduino Duemilanove includes two parts: command line interface and trigger logic.

Command Line Interface

The command line interface uses the serial port of the controller board to communicate with the other party, i.e., the client, for example, PC, and allows the client to perform various actions (through commands) and receive various events from the board (through notifications). The command line interface runs in the main flow. In the main loop of the firmware, t checks if any character comes to the serial port sent by the client. If a character is received, it adds to received ones, and check if they compose a complete command line. Once a complete command line is received, it tries to interpret the command, perform the command action, and reply to the client the execution result. If a complete command line is not yet received, or after a command reply is sent, it then checks if the notification queue has any pending notifications, and if any sends a notification to the client and removes it from the queue. When all notifications are sent, it goes back to check if there are any characters coming from the serial port.

The commands include:
Version command;
Start/stop triggering commands;
Notification enabling/disabling commands;
Hardware OPR manage ent commands;
Triggering parameter commands; and
Trigger output management commands.

Execution of commands often involves changing state or parameters of trigger logic. All commands will be replied with an execution result.

The notifications that the board can send actively to the client are:
OPR notification;
Hardware OPR Signal notification;
Trigger notification;
State change notification;
Hardware OPR timeout notification; and
Error notification.

Notifications are generated and enqueued by trigger logic.

Trigger Logic

The trigger logic manages hardware OPR and administers triggering. Trigger logic monitors if hardware OPR is available by tracking past hardware OPR signals. If the hardware OPR is not available, it does not allow triggering based on it, because that may appear hanging. In monitoring hardware OPR, hardware OPR event and hardware OPR timeout event may happen. Software OPR mode is always available, which uses a client specified OPR period to start triggering.

Initially the board is in "Idle" state. In executing start command, it goes to "Waiting" state if using hardware OPR mode, when next hardware OPR arrives, it goes to "Running" state and start triggering. If using software OPR mode, it directly goes to "Running" state and starts triggering. A stop command asks to go to "Idle" state. Any state change incurs a state change event.

Triggering is performed in a turn and is driven by a virtual OPR signal. The virtual OPR, could be a hardware OPR interrupt in hardware OPR mode, or software OPR request in software OPR mode. It then generates the triggers as specified by the parameters until a next OPR signal comes for next turn. In software OPR mode, next OPR is automatically generated by software. A new turn generates an OPR event.

Trigger logic starts a turn when an OPR happens. It uses the current OPR period, blade count, dwell and trim to determine each trigger's actual time in the turn, and tries to schedule Timer1 to expire at the specified time. When Timer1 expires, it receives an interrupt and generates a trigger pulse of specified length using Timer2. When a trigger is output, a trigger event is generated.

If trigger logic runs into error conditions, it can generate an error event.

All events are enqueued to the notification queue for the command line interface to send to the client, if that notification is not disabled. The access to the notification queue from triggering logic and main loop is synchronized to prevent data corruption.

ArduinoTrigger

ArduinoTrigger is the module running on the PC communicating with the Arduino board and its triggering firmware. ArduinoTrigger encapsulates the communication details and presents an interface that is easy to use.

The ArduinoTrigger synchronizes the command sent to and reply received from the Arduino controller, therefore, any command is returned with a reply. This greatly simplifies the use of ArduinoTrigger. A notification arriving in between is recognized and processed separately, and therefore does not interfere with the command reply. Any notification event can be dispatched if the user of ArduinoTrigger decides to subscribe to it with a call back function. Overall, ArduinoTrigger is an integral component with methods, properties and events representing triggering of a camera in a system as provided herein in accordance with an aspect of the present invention for making images of turbine blades.

In one embodiment of the present invention, the turbine with the rotating rotor with blades is operated off-line for test and/or maintenance, for instance. In that case the rotor is turned by an external source such as a motor at a speed of not faster than one revolution per minute in accordance with one preferred aspect of the present invention, or about or not faster than 3 revolutions per minute in accordance with a more preferred aspect of the present invention, or about or not faster than 6 revolutions per minute in accordance with an even more preferred aspect of the present invention, or about or not faster than 12 revolutions per minute in accordance with an even more preferred aspect of the present invention.

In accordance with an aspect of the present invention, the rotor has less than 30 blades attached. In accordance with another aspect of the present invention the rotor has less than 50 blades attached. In accordance with a further aspect of the present invention the rotor has less than 70 blades attached. In accordance with an aspect of the present invention the rotor has less than 100 blades attached. In accordance with an aspect of the present invention the rotor has at least 25 blades attached. In accordance with an aspect of the present invention the rotor has at least 50 blades attached.

Currently, digital cameras with a recording speed of 240 frames per second are quite common. Accordingly, it is well within the capabilities of current computers, controllers, OPR sensors and cameras to trigger and record images of all blades in an uninterrupted sequence of images of all adjacent blades at desired dwells.

In one embodiment of the preset invention, all blades in a sequence of images have the same offset or dwell. In one embodiment of the present invention, the dwell of images of adjacent blades taken in a sequence of images is different. In one embodiment of the present invention, more than one image is taken of a blade during a single turn of a rotor. For instance, two images are taken of a blade in a single turn with a first dwell and a second dwell.

Figure 6:
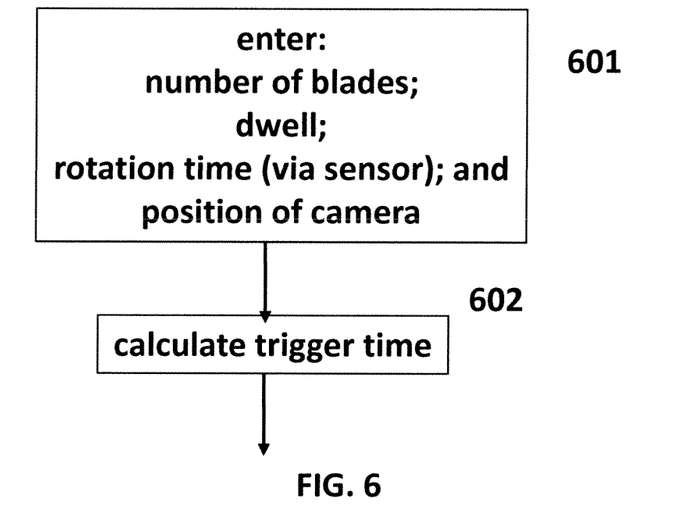
FIGS. 6-7 illustrate steps performed in accordance with an aspect of the present invention.

Steps provided in accordance with an aspect of the present invention are illustrated in FIG. 6. In a step 601 the number of blades, the desired dwell, and the position of the camera are all entered into a processor. One can enter an initial rotation time or the processor can determine a rotation time based on the OPR sensor input. Based on the input data in step 602 a trigger time for each blade is calculated by a processor. In accordance with an aspect of the present invention, a rotation time is entered into the processor and the processor controls a rotation source such as an electric motor to turn axis 105 at the desired rotation speed.

Figure 7:
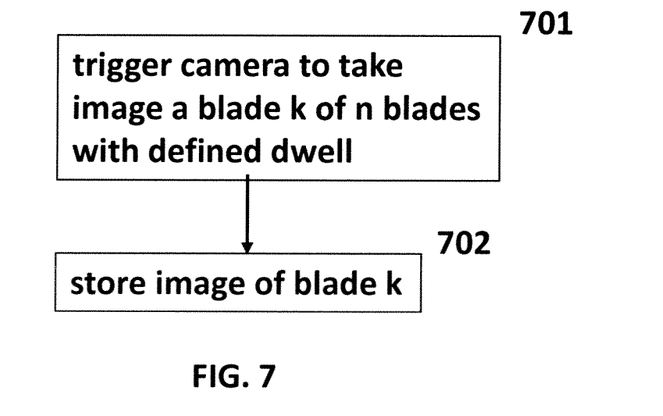

In step 701 in FIG. 7, the controller triggers the camera at the appropriate moments, based on the OPR trigger to take an image of blade k of n blades with the predefined dwell and of the preceding and succeeding blades on the rotor. In step 702, the image data of the blades is stored temporarily on a memory or on a permanent or semi-permanent data storage device such as a hard disk, an optical disk or a mass memory device such as a flash drive or the like. In addition to the above described mode of calculating when the camera should be triggered to take pictures of blades at the given dwell and in accordance with an embodiment of the present invention, the system is able to perform an additional capturing mode. Due to the uneven rotation speed within or beyond a turn, as well as possible moving of blades, the time instant calculated may not match the exact actual dwell of the blade. This may be caused by an unbalanced load on the axis of the rotor or by insufficient accuracy of the turning gear driving the rotation of the axis. The signal provided by the OPR sensor is in such situations not sufficient to provide sufficient precision for camera triggering. The dwell setting thus may be considered a dwell preset setting or a desired dwell that has to be approximated by additional steps.

Figure 8:
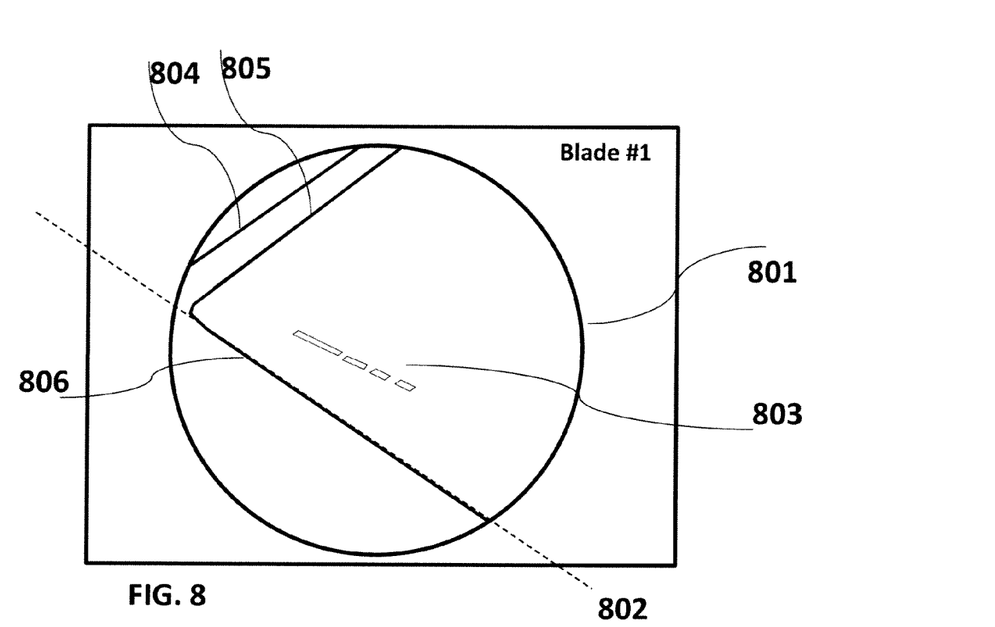
FIGS. 8-11 are diagrams illustrating images of a blade.
Figure 9:
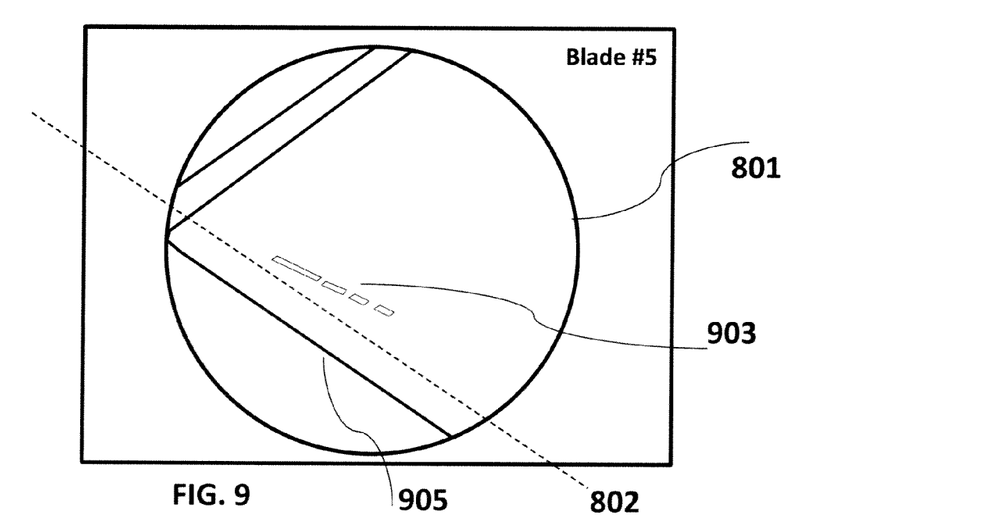
Figure 10:
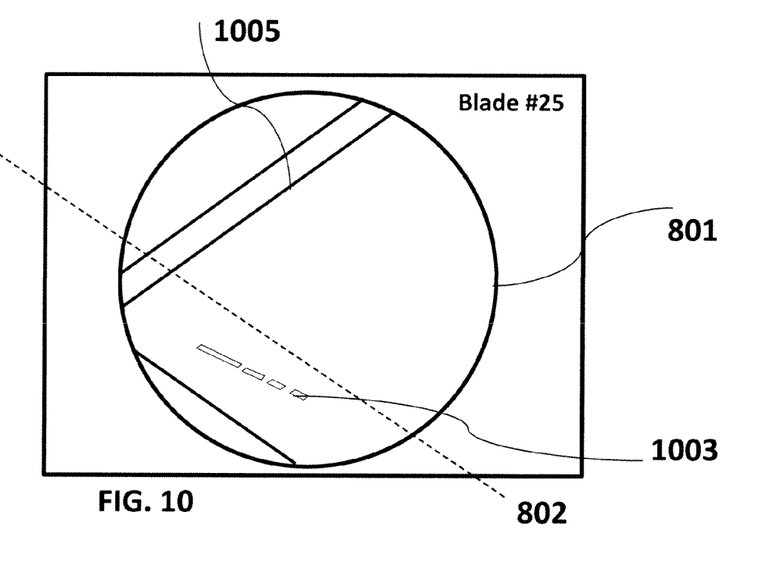
Figure 11:
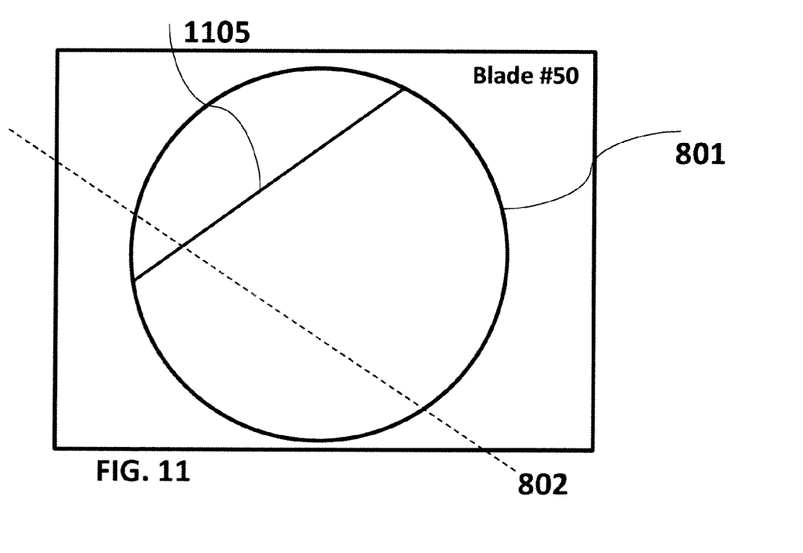

The rotational speed of the engine may thus turn out not to be uniform. From the perspective of captured images, the blades appear shifting positions relative to each other in the images even if they are taken using the same required dwell. This is illustrated in FIGS. 8-11. FIG. 8 is a diagram of an image of a blade (blade#1) taken through a porthole 801. A dwell line 802 is defined by an extracted edge 805 of the blade. Another edge 804 in the image is also shown. The blade has some pattern 803. All blades on the rotor may be assumed to be identical. FIGS. 9-11 are diagrams of images taken from blades #5, blade#25 and blade#50 using the same dwell wherein the trigger moment is calculated using the OPR signal and no further corrective measures.

FIG. 9 shows a diagram of the image of blade#5. One can see that the dwell line 802 and edge 905 are not aligned. The dwell line is closer to pattern 903 that with blade#1. FIG. 10 illustrates a further shift of the dwell line compared to edge 1005 and pattern 1003. In FIG. 11 there is additional shift in the dwell line. While an edge 1105 can be detected, no additional landmarks are visible.

To overcome this problem, image based methods are used, in accordance with an aspect of the present invention, to detect the relative blade shifting, and instruct the triggering device to take into account the necessary corrective offset, which is indicated herein with the term 'trim'. Trim is the additive adjustment for the ideal blade period, which is OPR period divided by blade count. By continuously monitoring the blade shift in images, estimate the trim, and adjust trigger delivery instant accordingly, the closed loop aims to stabilize the blade in image view for a given dwell even imperfect rotation of blades is present.

The image based blade shift detection uses common features of the blades, which include edges and corners. Such features are detected by known methods such as Canny edge detection and Harris corner detection, interest point detection (Harris-Affine). SIFT or any other image detection method that enables the detection of a feature in an image. After detecting a feature the new image of a blade #k can be aligned (registered) with a baseline image or an image of a previous blade. One will recognize that this allows the determination of an occurring shift and to tune the trigger timing. As an example, the edge 806 as shown in FIG. 8 may be used as a recognizable and extractable feature that can be used to register the images.

In one embodiment of the present invention, for each image, it detects these features. In yet another embodiment of the present invention the features are detected for each image that has been assigned a trigger moment and a dwell. Given two images taken consecutively, a processor compares the features from both images, and determines the relative movement of the blades in the camera. Depending on the position of the camera relative to the blades, the relative movement may appear in the image as a translation of the blade. This movement in the image coordinate system is then translated into the error of angular blade turning speed, and in the end trim $\Delta\alpha$, given camera calibration data and turbine machine model.

In one embodiment of the present invention, a trim $\Delta\alpha$ is determined from two consecutive images of a single blade while the blade is passing through the field of vision of the camera, wherein for each image a trigger moment and a dwell was determined. Using the feature extraction a trim $\Delta\alpha$ will be determined. In one embodiment of the present invention, the rotation speed of the blades is low enough that a camera is enabled to be triggered by the controller to take several images of a single blade as it rotates through the field of vision of the camera, even though only one image of a blade at a specific dwell is required. This allows the processor or controller to determine a trim $\Delta\alpha_k$ per sub-period $p=(t_{n+1}-t_n)/k$ when the time between two equivalent positions of two adjacent blades n and n+1 is divided into k intervals. This allows the processor or controller to calculate an overall trim $\Delta\alpha$ from at least intermediate trims $\Delta\alpha_k$ that are calculated between recordings of the desired images at moments $t_n$ and $t_{n+1}$ corrected for calculated trim.

In one embodiment of the present invention, the trim is calculated from at least two consecutive image recordings and applied to the next image recording to correct the trigger moment. Calculating the trim may also be based on earlier calculated trims. For instance, if a trim is a systematic phenomenon, for instance a shift in one direction or an oscillating shift or any shift that can be described by a predictive formula, the trim may be applied to an image recording based on a predicted or calculated trim.

In one embodiment of the present invention, an applied trim is based on the determined difference in trigger moment of at least two previous images using image analysis. In a further embodiment of the present invention an applied trim is based on the determined difference in trigger moment of more than two previous images using image analysis.

In one embodiment of the present invention, a trim that is applied is based on a processing of determined difference in trigger moments of more than two previous images using image analysis. For instance, the processor or controller can average previously determined trim values, extrapolate previous trim values or filter previously determined trim values, for instance by moving average filtering.

In one embodiment of the present invention, the trim is reset to 0 when the reference blade passes the OPR sensor.

Figure 12:
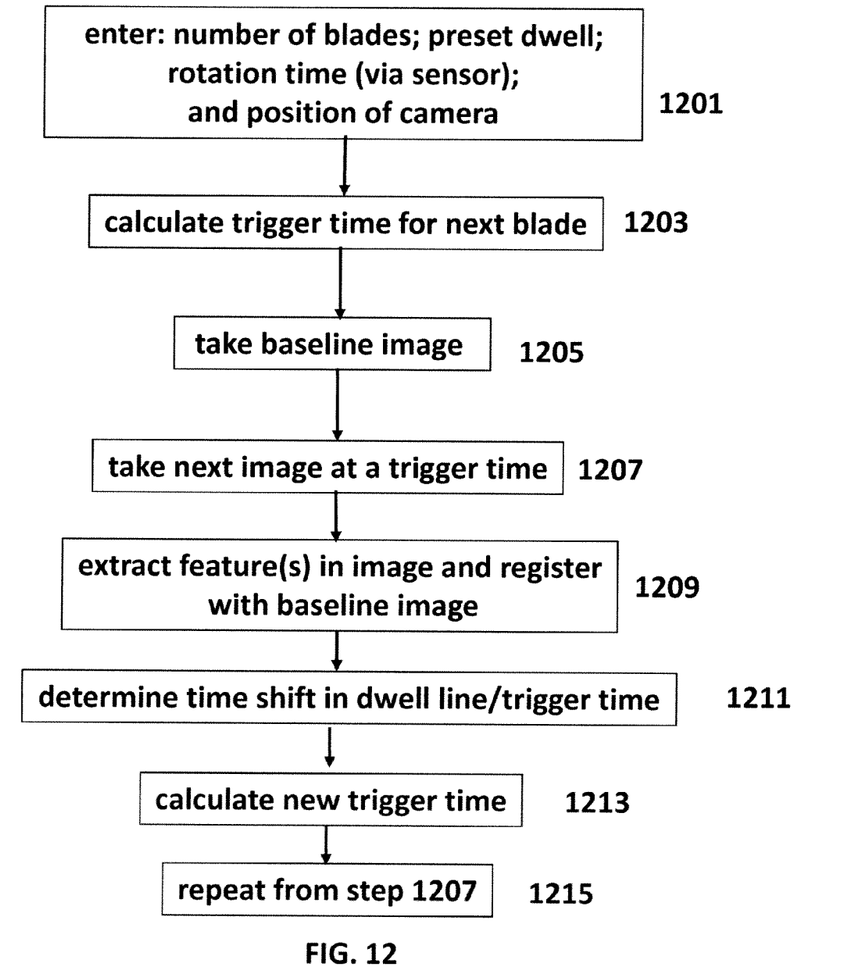
FIG. 12 illustrates steps performed in accordance with various aspects of the present invention.
Figure 13:
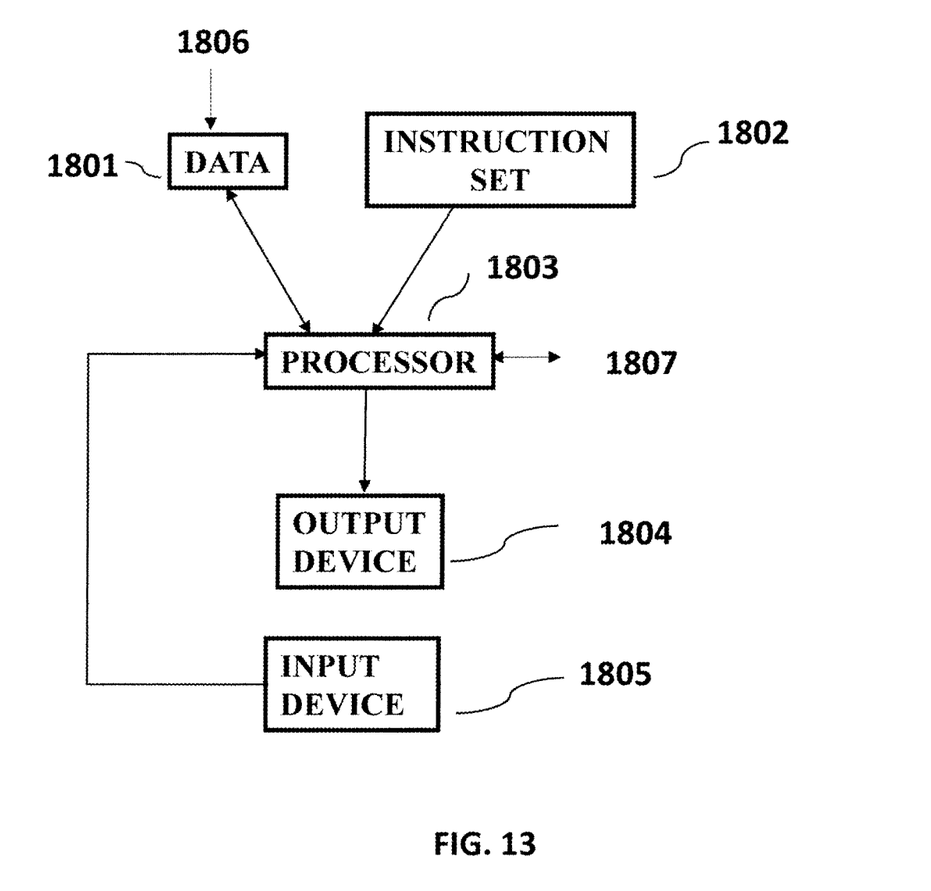
FIG. 13 illustrates a processor based system in accordance with an aspect of the present invention.

FIG. 12 illustrates at least one embodiment of trim correction. In step 1201, number of blades, dwell and rotation time are entered, or a rotation time is determined by the controller from the OPR sensor. Furthermore, one can provide the position of the camera relative to the OPR sensor, for instance. The controller may be instructed not to start taking images until a predefined number of OPR signals are received. In step 1203, the controller calculates an initial trigger time based on the data as provided or calculated from step 2101. A baseline image is taken in step 1205. The baseline image may be the image taken from the first blade passing through the field of view of the camera after the reference blade has passed the OPR sensor. In step 207, the next image of another blade is taken. In step 1209 features are extracted from this image to register the image with the baseline image. A time shift is determined relative to the baseline image in step 1211 and a new trigger time, adjusted for the time shift is calculated in step 1213. The previous steps as of step 1207, starting with taken an image at the adjusted trigger time are repeated. The steps may be repeated until the reference blade passes the OPR sensor and the method starts over again from step 1207, with the exception that the number of blades are already known and the dwell has already been set and one knows the relative position of the camera.

In one embodiment of the present invention, the blades are recorded when the rotor is driven by external gear with a rotation speed that is not greater than 3 rpm. The change in rotation of the blades in accordance with an aspect of the present invention, and illustrated by FIGS. 8-11, falls within about one blade captured by the camera within 25 blades of images. In one embodiment of the present invention, the controller can detect and correct a trigger moment shift of up to about ¼ blade in the field of vision of the camera between two consecutive blades at a rotating speed of 3 rpm or slower and the rotor having no more than 120 blades.

In a further embodiment of the present invention, the rotor speed, being not faster than 3 rpm, can be and is maintained in such a manner that the rotation time within a period T/n, wherein T is the rotation time of the rotor and n is the number of blades on the rotor does not change more than 10% within a single rotation and the controller is able to maintain an actual dwell of each image of each blade with an accuracy that is within 10% of the preset dwell setting. In a further embodiment of the present invention, the dwell correction method as provided herein in accordance with an aspect of the present invention provides an actual dwell for each of the images of each blade within a single rotation that is within 5% of the preset dwell setting.

The methods as provided herein are, in one embodiment of the present invention, implemented on a system or a computer device. Thus, steps described herein are implemented on a processor, as shown in FIG. 8. A system illustrated in FIG. 8 and as provided herein is enabled for receiving, processing and generating data. The system is provided with data that can be stored on a memory 1801. Data may be obtained from a sensor such as an OPR sensor or from any other data relevant source. Data may be provided on an input 1806. Such data may be trigger data or any other data that is helpful in a system as provided herein. The processor is also provided or programmed with an instruction set or program executing the methods of the present invention that is stored on a memory 1802 and is provided to the processor 1803, which executes the instructions of 1802 to process the data from 1801. Data, such as image data or any other data triggered or caused by the processor can be outputted on an output device 1804, which may be a display to display images or a data storage device. The processor also has a communication channel 1807 to receive external data from a communication device and to transmit data to an external device. The system in one embodiment of the present invention has an input device 1805, which may include a keyboard, a mouse, a pointing device, one or more cameras or any other device that can generate data to be provided to processor 1803.

The processor can be dedicated or application specific hardware or circuitry. However, the processor can also be a general CPU, a controller or any other computing device that can execute the instructions of 1802. Accordingly, the system as illustrated in FIG. 8 provides a system for processing data resulting from a sensor or any other data source and is enabled to execute the steps of the methods as provided herein as one or more aspects of the present invention.

In accordance with one or more aspects of the present invention methods and systems for triggering a camera for generating images of rotor blades on a rotating turbine rotor have been provided.

Thus, novel systems and methods and steps implementing the methods have been described and provided herein.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to and executed by, a machine comprising any suitable architecture.

It is to be understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

While there have been shown, described and pointed out fundamental novel features of the invention as applied to preferred embodiments thereof, it will be understood that various omissions and substitutions and changes in the form and details of the methods and systems illustrated and in its operation may be made by those skilled in the art without departing from the spirit of the invention. It is the intention, therefore, to be limited only as indicated by the scope of the claims.

The invention claimed is:

1. A method to determine a trigger moment for a controller controlled camera to record an image of a blade attached to a rotating rotor including a plurality of blades in a turbine, comprising:
   the controller controlled camera that is located outside the turbine and pointed at a porthole that provides only a partial view of a surface of the blade rotating through a field of view of the porthole;
   the turbine being operated in an offline condition, wherein the rotating rotor is driven by a motor;
   the controller determining a first trigger moment for the camera to capture the blade attached to the rotating rotor based on a number of the plurality of blades, a preset dwell that determines a part of the blade that is to appear on the image, a rotating speed of the rotating rotor and a position of the camera outside the turbine, the rotor rotating with a non-uniform speed within a single period of rotation;
   the camera recording and storing on a memory a first image of a first blade in the plurality of blades through the porthole in the turbine;
   the camera recording and storing on the memory a second image of a second blade in the plurality of blades through the porthole in the turbine;
   the controller registering the first and the second image based on a common feature in the first and second blades to determine a time shift; and
   the controller calculating the trigger moment for the blade from the first trigger moment adjusted based on the time shift to capture the part of the blade in accordance with the preset dwell.

2. The method as claimed in claim 1, further comprising:
   the controller controlled camera recording an image of the blade based on a trigger signal on the trigger moment determined by the controller.

3. The method as claimed in claim 1, wherein the common feature is extracted by using a feature extraction method from the group consisting of Canny edge detection, Harris corner detection, Harris-Affine interest point detection and SIFT.

4. The method of claim 1, further comprising determining a position of a reference blade with a once-per-revolution (OPR) sensor.

5. The method of claim 2, further comprising:
   the controller determining the trigger signal at each of a plurality of adjusted trigger moments; and
   the controller controlled camera recording at least a single image of each of the plurality of blades during a single rotation of the rotating rotor at the plurality of adjusted trigger moments.

6. The method of claim 5, wherein each of the at least single image of each of the number of blades recorded during the single rotation of the rotating rotor is provided with a data label and is stored as an individually retrievable image on a data storage device.

7. The method of claim 1, wherein the turbine is off-line and the rotating rotor is rotated by a motor.

8. The method of claim 1, wherein the rotating rotor rotates with a rotating speed of less than 12 revolutions per minute.

9. The method of claim 1, wherein the number of blades on the rotating rotor is less than 70.

10. The method of claim 1, wherein the controller maintains an actual dwell for each image of the plurality of blades within a single rotation of the rotor that is at least 10% accurate compared to the preset dwell.

11. A controller to trigger a camera to record an image of a blade attached to a rotating rotor with a plurality of blades in a turbine, comprising:
   a memory to store data;
   a processor enabled to execute instructions to perform the steps:
      determining a first trigger moment for the camera positioned outside the turbine to capture the blade attached to the rotating rotor through a porthole in the turbine, wherein the porthole allows only a partial view of a surface of the blade rotating through a field of view of the porthole, based on a number of the plurality of blades, a preset dwell that determines a part of the blade that is to appear on the image, a rotating speed of the rotating rotor and a position of the camera outside the turbine, the rotor rotating with a non-uniform speed within a single period of rotation;

the camera recording and storing on a memory a first image of a first blade in the plurality of blades through a porthole in the turbine;

the camera recording and storing on the memory a second image of a second blade in the plurality of blades through the porthole in the turbine;

the processor registering the first and the second image based on a common feature in the first and second blades to determine a time shift; and the processor calculating the trigger moment for the blade from the first trigger moment adjusted based on the time shift to capture the part of the blade in accordance with the preset dwell.

12. The controller as claimed in claim 11, further comprising:

the camera recording an image of the blade based on a trigger signal on the trigger moment.

13. The controller as claimed in claim 11, wherein the common feature is extracted by using a feature extraction method from the group consisting of Canny edge detection, Harris corner detection, Harris-Affine interest point detection and SIFT.

14. The controller as claimed in claim 11, further comprising determining a position of a reference blade with a once-per-revolution (OPR) sensor.

15. The controller as claimed in claim 12, further comprising:

the controller determining the trigger signal at each of a plurality of adjusted trigger moments; and the controller controlled camera recording at least a single image of each of the plurality of blades during a single rotation of the rotating rotor at the plurality of adjusted trigger moments.

16. The controller as claimed in claim 15, wherein each of the at least single image of each of the number of blades recorded during the single rotation of the rotating rotor is provided with a data label and is stored as an individually retrievable image on a data storage device.

17. The controller as claimed in claim 11, wherein the turbine is off-line and the rotating rotor is rotated by a motor.

18. The controller as claimed in claim 11, wherein the rotating rotor rotates with a rotating speed of less than 12 revolutions per minute.

19. The controller as claimed in claim 11, wherein the number of blades on the rotating rotor is less than 70.

20. The controller as claimed in claim 11, wherein the processor maintains an actual dwell for each image of the plurality of blades within a single rotation of the rotor that is at least 10% accurate compared to the preset dwell.

* * * * *